US006168852B1

(12) United States Patent
Smith, III et al.

(10) Patent No.: US 6,168,852 B1
(45) Date of Patent: Jan. 2, 2001

(54) WIPES HAVING A SUBSTRATE WITH A DISCONTINUOUS PATTERN OF A HIGH INTERNAL PHASE INVERSE EMULSION DISPOSED THEREON AND PROCESS OF MAKING

(75) Inventors: Charles Zell Smith, III, Loveland; Steven Lee Barnholtz, Hamilton; David William Cabell, Cincinnati, all of OH (US)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/267,133

(22) Filed: Feb. 16, 1999

Related U.S. Application Data (63) Continuation of application No. 08/909,449, filed on Aug. 11, 1997, now Pat. No. 5,914,177.

(51) Int. Cl.$^7$ .................. B32B 3/00; B05D 5/00
(52) U.S. Cl. ............... 428/201; 428/211; 442/381; 162/124; 162/164.1; 427/286; 427/288
(58) Field of Search .................. 162/172, 179, 162/124, 164.1; 428/195, 201, 211; 427/286, 288; 442/381

(56) References Cited

U.S. PATENT DOCUMENTS

| | | | |
|---|---|---|---|
| 3,965,518 | 6/1976 | Muolo | 15/104.93 |
| 4,097,965 | 7/1978 | Gotchel et al. | 19/306 |
| 4,191,609 | 3/1980 | Trokhan | 162/113 |
| 4,226,903 | 10/1980 | Gottung et al. | 428/195 |
| 4,296,161 | 10/1981 | Kaiser et al. | 428/171 |
| 4,300,981 | 11/1981 | Carstens | 162/109 |
| 4,426,418 | 1/1984 | Coleman et al. | 428/211 |
| 4,481,243 | 11/1984 | Allen | 428/154 |
| 4,513,051 | 4/1985 | Lavash | 428/212 |
| 4,514,345 | 4/1985 | Johnson et al. | 264/22 |
| 4,637,859 | 1/1987 | Trokhan | 162/109 |
| 5,143,776 | 9/1992 | Givens | 428/194 |
| 5,245,025 | 9/1993 | Trokhan et al. | 536/56 |
| 5,277,761 | 1/1994 | Van Phan et al. | 162/109 |
| 5,328,565 | 7/1994 | Rasch et al. | 162/113 |
| 5,503,715 | 4/1996 | Trokhan et al. | 162/296 |
| 5,534,326 | 7/1996 | Trokhan et al. | 428/131 |
| 5,609,725 | 3/1997 | Van Phan | 162/117 |
| 5,628,876 | 5/1997 | Ayers et al. | 162/358.2 |
| 5,637,194 | 6/1997 | Ampulski et al. | 162/109 |
| 5,756,112 | 5/1998 | Mackey | 424/402 |
| 5,759,928 | 6/1998 | Harper | 428/195 |
| 5,763,332 | 6/1998 | Gordon et al. | 442/84 |

FOREIGN PATENT DOCUMENTS

| | | |
|---|---|---|
| 76 19 792 U | 3/1977 | (DE) . |
| 0 211 773 | 2/1987 | (EP) . |
| 2 353 265 | 12/1977 | (FR) . |
| WO 96/14835 | 5/1996 | (WO) . |
| WO 96/21505 | 7/1996 | (WO) . |
| WO 97/40815 | 11/1997 | (WO) . |

*Primary Examiner*—Christopher Raimund
(74) *Attorney, Agent, or Firm*—Larry L. Huston; Donald E. Hasse; Caroline Wei-Berk (57) ABSTRACT

A wipe comprising a high internal phase inverse emulsion disposed in a discontinuous pattern on a substrate. The pattern provides areas coated with the emulsion and areas free of the emulsion. Preferably the emulsion is disposed so that the surface area to volume ratio of the emulsion is minimized. The emulsion locally expresses water during use upon the application of pressure to the wipe. The water is useful for cleaning. The discontinuous pattern of the emulsion provides regions of the substrate which are wetted during use and regions which may remain dry. The wetted regions transfer water to the surface to be cleaned. The dry regions then remove the water from the surface for more efficacious cleaning.

11 Claims, 3 Drawing Sheets

WIPES HAVING A SUBSTRATE WITH A DISCONTINUOUS PATTERN OF A HIGH INTERNAL PHASE INVERSE EMULSION DISPOSED THEREON AND PROCESS OF MAKING

This is a continuation of application Ser. No. 08/909,449 filed on Aug. 11, 1997, now U.S. Pat. No. 5,914,177.

FIELD OF THE INVENTION

The present invention is related to cleaning articles, particularly wipes having a high internal phase inverse emulsion disposed on a substrate.

BACKGROUND OF THE INVENTION

Substrates having lotions and other coatings are well known in the art. Lotions are often in conjunction with substrates to soften the substrate. Lotions can also be used to soothe the skin when the substrate is used, for example, as a facial tissue. Examples of substrates having lotion and useful in the facial tissue art are found in U.S. Pat. No. 4,426,418, issued Jan. 17, 1984 to Coleman et al. and commonly assigned U.S. Pat. No. 4,481,243, issued Nov. 6, 1984 to Allen, the disclosure of which Allen patent is incorporated herein by reference.

However, these attempts in the art do not solve the problem of how to use the lotion to improve cleaning of the skin with the tissue. Nor do these attempts show how to clean other surfaces using a substrate treated with a lotion.

Products, such as wipes, have been developed. Certain wipes have a significant advantage over earlier prior art cleaning products for removing soiling, particularly from the perianal region. Such wipes comprise a substrate (e.g., a nonwoven or tissue) treated with a water-in-lipid emulsion. Such wipes are particularly advantageous for cleaning, especially when provided in the form of wet-like cleansing wipes used to remove perianal soils. Examples of such wipes and their manufacture are found in commonly assigned World Patent Applications WO 96/14835, published May 23, 1996, in the names of Mackey et al.; and WO 96/21505, published July 18, 1996, in the name of DesMarais, the disclosures of which are incorporated herein by reference. These wipes release significant quantities of water during use for comfortable, more effective cleaning.

The lipid phase of the emulsion found in these wipes is sufficiently brittle so as to be easily disrupted by low shear contact or compression (e.g., during the wiping of the skin) to readily release this internal water phase, but sufficiently tough at elevated temperatures where the lipid is melted to avoid premature release of the water phase during the rigors of processing. The continuous lipid phase of these articles is also sufficiently stable during storage so as to prevent significant evaporation of the internal water phase. The normal tensile strength and flushability properties of these articles are not adversely affected when treated with the high internal phase inverse emulsions of the present invention. As a result, users of these articles get comfortable, efficient, moist cleaning without having to change their normal cleaning habits. This technology is readily useful for other purposes, such as cleaning hard surfaces, etc.

The cleaning process becomes easier if the emulsion is directly exposed to the surface to be cleaned. Such a wipe may comprise a substrate having one or two exposed, outwardly facing surfaces, and the emulsion disposed on one of the exposed surfaces. However, such an embodiment provides the disadvantages of imparting a tacky feel to the user, potential loss of emulsion from the surface, and difficulties in processing. In a preferred embodiment, the emulsion is disposed between two plies of the substrate to yield a laminate.

It has unexpectedly been found that a continuous coating of the emulsion on the substrate does not provide the most efficacious cleaning, particularly when it is desired to clean human skin. A discontinuous pattern of the emulsion on the substrate provides a cleaning mechanism not found in the prior art. As used herein, a discontinuous pattern of the emulsion is a pattern having regions of the substrate free of the emulsion intermediate regions of the substrate upon which the emulsion is disposed.

During cleaning, water is released from the emulsion to remove dirt from the skin. The area of the skin wetted by the water and from which dirt is removed is then wiped dry with the regions of the substrate free of the emulsion. Similar benefits occur when the wipe is used to clean other surfaces, such as window glass, countertops, sinks, porcelain and metal fixtures, walls and the like, and from other surfaces, such as carpeting or furniture.

The mechanism to transfer the water from the emulsion to the surface to be cleaned involves several steps. First, the water is released or expressed from the emulsion due to pressure imparted by the user. The pressure ruptures the emulsion, freeing the water. The water then saturates the substrate. Upon saturation, the water penetrates the substrate in the Z-direction. Excess water, which is that water in excess of the local absorbent capacity of the substrate then is transferred from the wipe to the surface.

One potential approach to the problem of providing sufficient quantities of water to saturate the substrate and transfer the water to the surface is to dispose a continuous layer of emulsion on the substrate. A continuous layer of emulsion may contain a greater quantity of water than a discontinuous layer of the emulsion. This potential approach has several drawbacks. First, a thin continuous layer of emulsion may not exceed the local capacity of the substrate. Second, excessive lipid phase in the emulsion causes a build up and may not be well received by the user and contribute to manufacturing difficulties. Third, if the amount of the emulsion becomes too great, it can be difficult to rupture the emulsion and release the water therefrom. Such difficulty occurs due to a greater quantity of the lipid phase being present. As the amount of lipid phase increases, slippage of the emulsion relative to itself occurs, rather than rupture of the emulsion. Fourth, the surface area to volume ratio is far from optimal. Finally, the cost of the wipe increases directly with the amount of emulsion provided.

Accordingly, it is an object of the present invention to provide a wipe comprising a substrate and a high internal phase inverse emulsion. It is further an object of the present invention to provide such a wipe having a discontinuous coating of the emulsion on the substrate. It is finally an object of the present invention to provide a wipe having such an emulsion disposed in a pattern that provides improved transmission of water released from the emulsion to the surface desired to be cleaned, while at the same time minimizing loss of such water from the emulsion due to evaporation.

SUMMARY OF THE INVENTION

The invention comprises a wipe. The wipe comprises a substrate and a high internal phase inverse emulsion disposed thereon. The emulsion is disposed in a discontinuous pattern so that the substrate has first regions coated with the emulsion and second regions free of the emulsion.

In a preferred embodiment, the substrate comprises high and low basis weight regions. The emulsion is juxtaposed with the low basis weight regions.

DETAILED DESCRIPTION OF THE INVENTION

The wipe disclosed herein may be used for several purposes. For example, the wipe may be used as a facial tissue, bath tissue, paper towel, a baby wipe, an adult wipe, a hard surface cleaner, etc. The intended use of the wipe does not limit the final product.

The Substrate

Figure 1:
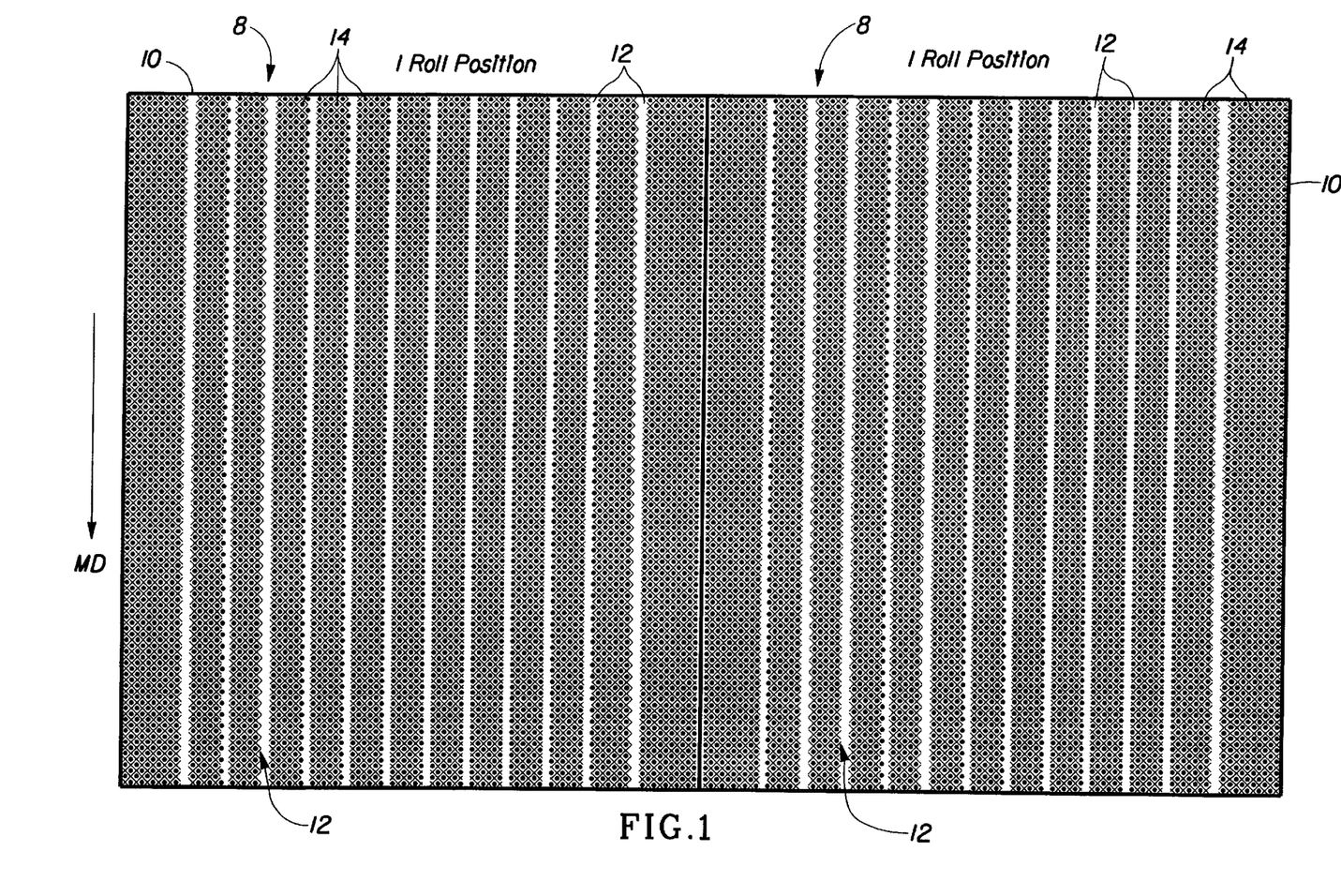
FIG. 1 is a top plan view of a wipe according to the present invention showing two roll positions.

Referring to FIG. 1, the wipe 8 comprises a substrate 10 and an emulsion 12 disposed thereon. The substrate 10 may be cellulosic, particularly a tissue, a nonwoven, a foam, or any combination thereof. Suitable cellulosic substrates 10 are described in U.S. Pat. No. 5,245,025, issued Sep. 14, 1993 to Trokhan et al.; U.S. Pat. No. 5,503,715, issued Apr. 2, 1996 to Trokhan et al.; U.S. Pat. No. 5,534,326, issued Jul. 9, 1996 to Trokhan et al.; U.S. Pat. No. 4,637,859 issued Jan. 20, 1987 to Trokhan; U.S. Pat. No. 4,514,345, issued Apr. 30, 1985 to Johnson et al.; U.S. Pat. No. 4,529,480, issued Jul. 16, 1985 to Trokhan; U.S. Pat. No. 5,328,565, issued Jul. 12, 1994 to Rasch et al.; U.S. Pat. No. 4,191,609, issued Mar. 4, 1980 to Trokhan; U.S. Pat. No. 4,300,981, issued Nov. 17, 1981 to Carstens; U.S. Pat. No. 4,513,051, issued Apr. 23, 1985 to Lavash; U.S. Pat. No. 4,637,859, issued Jan. 20, 1987 to Trokhan; U.S. Pat. No. 5,143,776, issued Sep. 1, 1992 to Givens; U.S. Pat. No. 5,637,194, issued Jun. 10, 1997 to Ampulski et al.; U.S. Pat. No. 5,609.725, issued Mar. 11, 1997 to Phan; and U.S. Pat. No. 5,628,876, issued May 13, 1997 to Ayers et al., the disclosures of which patents are incorporated herein by reference.

A suitable tissue substrate 10 has a basis weight of about 7 to 25 pounds per 3,000 square feet per ply, preferably about 8 to 10 pounds per 3,000 square feet per ply, and most preferably about 8½ pounds per 3,000 square feet per ply for bath tissue applications, and about 18 to 22 pounds per 3,000 square feet per ply for hard surface cleaning applications. A multi-basis weight substrate 10 is feasible for the claimed invention. A multi-basis weight substrate 10 has regions of high and low basis weight juxtaposed together, and optionally intermediate basis weight regions. The high basis weight regions provide strength. The low basis weight regions provide for transfer of water released from the emulsion to the surface. In a degenerate case, the low basis weight regions may be apertures, to increase the transfer of water to the surface. If a multi-basis weight substrate 10 is used, the macro-basis weight of the substrate 10, averaging both high and low basis weight regions or high, intermediate and low basis weight regions, is considered.

If a multi-basis weight substrate 10 is desired, such a substrate 10 may be made according to commonly assigned U.S. Pat. No. 5,277,761, issued Jan. 11, 1994 to Phan et al.; U.S. Pat. No. 5,443,691, issued Aug. 22, 1995 to Phan et al.; and U.S. Pat. No. 5,614,061, issued Mar. 25, 1997 to Phan et al., the disclosures of which patents are incorporated herein by reference. If a multi-basis weight substrate 10 having radially oriented fibers is desired, such a substrate 10 may be made according to commonly assigned U.S. Pat. Nos. 5,245,025, issued Sep. 14, 1993 to Trokhan et al.; U.S. Pat. No. 5,503,715, issued Apr. 2, 1996 to Trokhan et al.; U.S. Pat. No. 5,527,428, issued Jun. 18, 1996 to Trokhan et al.; or U.S. Pat. No. 5,534,326, issued Jul. 9, 1996 to Trokhan et al., the disclosures of which patents are incorporated herein by reference.

If one desires to use a more durable or nonwoven substrate 10 for a wipe 8, such a substrate 10 may be made according to commonly owned U.S. Pat. Nos. 4,097,965, issued Jul. 4, 1978 to Gotchel et al.; U.S. Pat. No. 4,130,915, issued Dec. 26, 1978 to Gotchel et al.; U.S. Pat. No. 4,296,161, issued Oct. 20, 1981 to Kaiser et al.; and U.S. Pat. No. 4,682,942, issued Jul. 28, 1987 to Gotchel et al., the disclosures of which patents are incorporated herein by reference.

The Emulsion

The emulsion 12 comprises: (1) a continuous solidified lipid phase; (2) an emulsifier that forms the emulsion 12 when the lipid phase is fluid; and (3) an internal polar phase dispersed in the lipid phase. This emulsion 12 ruptures when subjected to low shear during use, e.g., wiping of the skin or other surface, so as to release the internal polar phase.

1. External Lipid Phase

The continuous solidified lipid phase provides the essential stabilizing structure for the high internal phase inverse emulsions 12 of the present invention. In particular, this continuous lipid phase is what keeps the dispersed internal phase from being prematurely released prior to use of the article, such as during storage.

The continuous lipid phase can comprise from about 2 to about 60% of the emulsion 12 of the present invention. Preferably, this continuous lipid phase will comprise from about 5 to about 30% of the emulsion 12. Most preferably, this lipid phase will comprise from about 6 to about 15% of the emulsion 12.

The major constituent of this continuous lipid phase is a waxy lipid material. This lipid material is characterized by a melting point of about 30° C. or higher, i.e., is solid at ambient temperatures. Preferably, the lipid material has a melting point of about 50° C. or higher. Typically, the lipid material has a melting point in the range of from about 40° to about 80° C., more typically in the range of from about 50° to about 70° C.

Although this waxy lipid material is solid at ambient temperatures, it also needs to be fluid or plastic at those temperatures at which the high internal phase inverse emulsion 12 is applied to the carrier. Moreover, even though the lipid material is fluid or plastic at those temperatures at which the emulsion 12 is applied to the carrier substrate 10, it should still desirably be somewhat stable (i.e., minimal coalescence of emulsion 12 micro-droplets) for extended periods of time at elevated temperatures (e.g., about 50° C. or higher) that are normally encountered during storage and distribution of the articles of the present invention. This lipid material also needs to be sufficiently brittle at the shear conditions of use of the article such that it ruptures and releases the dispersed internal polar phase. These lipid materials should also desirably provide a good feel to the skin when used in personal care products such as wet-like cleansing wipes 8 and tissue used in perianal cleaning.

Suitable waxy lipid materials for use in the high internal phase inverse emulsion 12 of the present invention include natural and synthetic waxes, as well as other oil soluble materials having a waxy consistency. As used herein, the term "waxes" refers to organic mixtures or compounds that are generally water-insoluble and tend to exist as amorphous or microcrystalline or crystalline solids at ambient temperatures (e.g., at about 25° C.). Suitable waxes include various types of hydrocarbons, as well as esters of certain fatty acids and fatty alcohols. They can be derived from natural sources (i.e., animal, vegetable or mineral) or they can be synthesized. Mixtures of these various waxes can also be used.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes.

Besides the waxy lipid material, the continuous lipid phase can include minor amounts of other lipophilic or lipid-miscible materials. These other lipophilic/lipid-miscible materials are typically included for the purpose of stabilizing the emulsion 12 to minimize loss of the internal polar phase or for improving the aesthetic feel of the emulsion 12 on the skin. Suitable materials of this type that can be present in the continuous lipid phase include hot melt adhesives such as Findley 193-336 resin, long chain alcohols such as cetyl alcohol, stearyl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharide polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinbefore described groups having a fluid consistency at or below about 37° C. By "solid polyol polyester" is meant a polyol polyester from the hereinbefore described groups having a plastic or solid consistency at or above about 37° C. Liquid polyol polyesters and solid polyol polyesters may be successfully employed as emollients and immobilizing agents, respectively, in emulsions 12 of the present invention. In some cases, solid polyol polyesters may also provide some emolliency functionality.

2. Internal Polar Phase

Typically, the major component of the high internal phase inverse emulsions 12 of the present invention is the dispersed internal polar phase. 11 >In preferred embodiments, the polar phase will contain a significant percentage of water, preferably at least about 60%, by weight of the emulsion 12, more preferably at least about 75%, by weight, still more preferably at least about 90%, by weight.

The internal polar phase can provide a number of different benefits when released. For example, in wet-like cleaning wipes 8 for perianal cleaning where the internal polar phase is water, it is this released water that provides the primary cleansing action for these wipes 8.

In a preferred embodiment of the present invention, the internal polar phase (preferably comprising water as a major constituent) is a disinfecting polar phase comprising an antimicrobial compound, preferably an essential oil or an active thereof, and a bleach, preferably a peroxygen bleach. Disinfecting wipes 8 comprising such an internal disinfecting polar phase provide effective disinfecting performance on a surface while being safe to the surface treated.

By "effective disinfecting performance" it is meant herein that the disinfecting wipes 8 of the present invention allow significant reduction in the amount of bacteria on an infected surface. Indeed, effective disinfection may be obtained on various microorganisms including Gram positive bacteria like Staphylococcus aureus, and Gram negative bacteria like Pseudomonas aeruginosa, as well as on more resistant micro-organisms like fungi (e.g., Candida albicans) present on infected surfaces.

Another advantage of the disinfecting wipes 8 according to the present invention is that besides the disinfection properties delivered, good cleaning is also provided as the disinfecting polar phase may further comprise surfactants and/or solvents.

An essential element of the preferred internal disinfecting polar phase is an antimicrobial compound typically selected from the group consisting of an essential oil and an active thereof, paraben (e.g., methyl paraben, ethyl paraben), glutaraldehyde and mixtures thereof. Essential oils or actives thereof are the preferred antimicrobial compounds to be used herein.

Suitable essential oils or actives thereof to be used herein are those essential oils which exhibit antimicrobial activity and more particularly antibacterial activity. By "actives of essential oils" it is meant herein any ingredient of essential oils that exhibits antimicrobial/antibacterial activity. A further advantage of said essential oils and actives hereof is that they impart pleasant odor to the disinfecting wipes 8 according to the present invention without the need of adding a perfume. Indeed, the disinfecting wipes 8 according to the present invention deliver not only excellent disinfecting performance on infected surfaces but also good scent.

Such essential oils include, but are not limited to, those obtained from thyme, lemongrass, citrus, lemons, oranges, anise, clove, aniseed, cinnamon, geranium, roses, mint, lavender, citronella, eucalyptus, peppermint, camphor, sandalwood and cedar and mixtures thereof. Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, terpineol, limonene, methyl salycilate and mixtures thereof. Preferred actives of essential oils to be used herein are thymol, eugenol, verbenone, eucalyptol, carvacrol, limonene and/or geraniol. Thymol may be commercially available for example from Aldrich, eugenol may be commercially available for example from Sigma, Systems—Bioindustries (SBI)—Manheimer Inc.

Typically, the antimicrobial compound or mixtures thereof will be present in the internal polar phase at a level of from 0.001% to 5%, preferably from 0.001% to 3%, more preferably from 0.005% to 1%, by weight of total internal polar phase.

An important element of the internal disinfecting polar phase is a bleach or mixtures thereof. Any bleach known to those skilled in the art may be suitable to be used herein including any chlorine bleach as well as any peroxygen bleach. The presence of the bleach, preferably the peroxygen bleach, in the disinfecting wipes 8 of the present invention contribute to the disinfection properties of the wipes 8.

Suitable chlorine bleaches to be used herein include any compound capable of releasing chlorine when said compound is in contact with water. Suitable chlorine bleaches include alkali metal dichloroisocyanurates as well as alkali metal hypohalites like hypochlorite and/or hypobromite. Preferred chlorine bleaches are alkali metal hypochlorites. Various forms of alkali metal hypochlorite are commercially available, for instance sodium hypochlorite.

Preferred bleaches for use herein are peroxygen bleaches, more particularly hydrogen peroxide, or a water soluble source thereof, or mixtures thereof. Hydrogen peroxide is particularly preferred.

Peroxygen bleaches like hydrogen peroxide are preferred herein as they are generally well accepted from an environmental point of view. For example the decomposition products of hydrogen peroxide are oxygen and water.

As used herein, a hydrogen peroxide source refers to any compound which produces perhydroxyl ions when said compound is in contact with water. Suitable water-soluble sources of hydrogen peroxide for use herein include percarbonates, persilicates, persulphates such as monopersulfate, perborates, peroxyacids such as diperoxydodecandioic acid (DPDA), magnesium perphthalic acid, dialkylperoxides, diacylperoxides, performed percarboxylic acids, organic and inorganic peroxides and/or hydroperoxides and mixtures thereof.

Typically, the bleach or mixtures thereof is present at a level of from 0.001% to 15% by weight of the total internal polar phase, preferably from 0.001% to 5%, and more preferably from 0.005% to 2%.

The internal disinfecting polar phase may further comprise a detersive surfactant or a mixture thereof. Typically, the surfactant or mixtures thereof is present at a level of from 0.001% to 40% by weight of the total internal polar phase, preferably from 0.01% to 10% and more preferably from 0.05% to 2%.

Suitable detersive surfactants to be used in the present invention include any surfactant known to those skilled in the art like nonionic, anionic, cationic, amphoteric and/or zwitterionic surfactants. Preferred detersive surfactants to be used herein are the amphoteric and/or zwitterionic surfactants.

Suitable amphoteric detersive surfactants to be used herein include amine oxides of the formula $R^1R^2R^3NO$, wherein each of $R^1$, $R^2$ and $R^3$ is independently a saturated, substituted or unsubstituted, linear or branched hydrocarbon chain having from 1 to 30 carbon atoms. Preferred amine oxide surfactants to be used according to the present invention are amine oxides of the formula $R^1R^2R^3NO$, wherein $R^1$ is an hydrocarbon chain having from 1 to 30 carbon atoms, preferably from 6 to 20, more preferably from 8 to 16, most preferably from 8 to 12, and wherein $R^2$ and $R^3$ are independently substituted or unsubstituted, linear or branched hydrocarbon chains having from 1 to 4 carbon atoms, preferably from 1 to 3 carbon atoms, and more preferably are methyl groups. $R^1$ may be a saturated, substituted or unsubstituted, linear or branched hydrocarbon chain. Suitable amine oxides for use herein are for instance natural blend $C_8$–$C_{10}$ amine oxides as well as $C_{12}$–$C_{16}$ amine oxides commercially available from Hoechst. Amine oxides are preferred herein as they deliver effective cleaning performance and further participate to the disinfecting properties of the disinfecting wipes 8 herein.

Suitable zwitterionic surfactants to be used herein contain both cationic and anionic hydrophilic groups on the same molecule at a relatively wide range of pH's. The typical cationic group is a quaternary ammonium group, although other positively charged groups like phosphonium, imidazolinium and sulfonium groups can be used. The typical anionic hydrophilic groups are carboxylates and sulfonates, although other groups such as sulfates, phosphonates, and the like can be used. A generic formula for some zwitterionic surfactants to be used herein is $$R^1-N^+(R^2)(R^3)R^4\ [X^-]$$

wherein $R^1$ is a hydrophobic group; $R^2$ and $R^3$ are each $C_1$–$C_4$ alkyl, hydroxy alkyl or other substituted alkyl group which can also be joined to form ring structures with the N; $R^4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R^1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, derivatives thereof or mixtures thereof. Said betaine or sulphobetaine surfactants are preferred herein as they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., hard surfaces in contact with food and/or babies. Betaine and sulphobetaine surfactants are also extremely mild to the skin is and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and

2,255,082, incorporated herein by reference. Preferred betaine and sulphobetaine surfactants herein are according to the formula wherein R¹ is a hydrocarbon chain containing from 1 to 24 carbon atoms, preferably from 8 to 18, more preferably from 12 to 14, wherein R² and R³ are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of R¹, R² and R³ hydrocarbon chains is from 14 to 24 carbon atoms, or mixtures thereof.

Examples of particularly suitable betaine surfactants include $C_{12}$–$C_{18}$ alkyl dimethyl betaine such as coconutbetaine and $C_{10}$–$C_{16}$ alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

or wherein each R¹ is a hydrocarbon, e.g. an alkyl group containing from 8 up to 20, preferably up to 18, more preferably up to 16 carbon atoms, each R² is either a hydrogen (when attached to the amido nitrogen), short chain alkyl or substituted alkyl containing from 1 to 4 carbon atoms, preferably groups selected from the group consisting of methyl, ethyl, propyl, hydroxy substituted ethyl or propyl and mixtures thereof, preferably methyl, each R³ is selected from the group consisting of hydrogen and hydroxy groups and each n is a number from 1 to 4, preferably from 2 to 3, more preferably 3, with no more than one hydroxy group in any $(C(R^3)_2)$ moiety. The R₁ groups can be branched and/or unsaturated. The R² groups can also be connected to form ring structures. A surfactant of this type is a $C_{10}$–$C_{14}$ fatty acylamidopropylene-(hydroxypropylene)sulfobetaine that is available from the Sherex Company under the trade name "Varion CAS sulfobetaine®.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Particularly suitable for use herein as nonionic surfactants are the hydrophobic nonionic surfactants having an HLB (hydrophilic-lipophilic balance) below 16 and more preferably below 15. Those hydrophobic nonionic surfactants have been found to provide good grease cutting properties.

Preferred nonionic surfactants for use herein are nonionic surfactants according to the formula RO—$(C_2H_4O)_n$ $(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and n and m are from 0.5 to 15, more preferably n+m is from 1 to 10 and n and m are from 0 to 10. The preferred R chains for use herein are the $C_8$ to $C_{22}$ alkyl chains. Accordingly, suitable hydrophobic nonionic surfactants for use herein are Dobanol R 91-2.5 (HLB=8.1; R is a mixture of $C_9$ and $C_{11}$ alkyl chains, n is 2.5 and m is 0), or Lutensol R TO3 (HLB=8; R is a C13 alkyl chains, n is 3 and m is 0), or Lutensol R AO3 (HLB=8; R is a mixture of $C_{13}$ and $C_{15}$ alkyl chains, n is 3 and m is 0), or Tergitol R 25L3 (HLB=7.7; R is in the range of $C_{12}$ to $C_{15}$ alkyl chain length, n is 3 and m is 0), or Dobanol R 23-3 (HLB=8.1; R is a mixture of $C_{12}$ and $C_{13}$ alkyl chains, n is 3 and m is 0), or Dobanol R 23-2 (HLB=6.2; R is a mixture of $C_{12}$ and $C_{13}$ alkyl chains, n is 2 and m is 0), or Dobanol R 45-7 (HLB=11.6; R is a mixture of $C_{14}$ and $C_{15}$ alkyl chains, n is 7 and m is 0) Dobanol R 23-6.5 (HLB=11.9; R is a mixture of $C_{12}$ and $C_{13}$ alkyl chains, n is 6.5 and m is 0), or Dobanol R 25-7 (HLB=12; R is a mixture Of $C_{12}$ and $C_{15}$ alkyl chains, n is 7 and m is 0), or Dobanol R 91-5 (HLB=11.6; R is a mixture of $C_9$ and $C_{11}$ alkyl chains, n is 5 and m is 0), or Dobanol R 91-6 (HLB=12.5; R is a mixture of $C_9$ and $C_{11}$ alkyl chains, n is 6 and m is 0), or Dobanol R 91-8 (HLB=13.7; R is a mixture of $C_9$ and $C_{11}$ alkyl chains, n is 8 and m is 0), Dobanol R 91-10 (HLB=L14.2; R is a mixture of $C_9$ to $C_{11}$ alkyl chains, n is 10 and m is 0), or mixtures thereof. Preferred herein are Dobanol R 91-2.5, or Lutensol R TO3, or Lutensol R AO3, or Tergitol R 25L3, or Dobanol R 23-3, or Dobanol R 23-2, or Dobanol R 23-10, or mixtures thereof. DobanolR surfactants are commercially available from SHELL. LutensolR surfactants are commercially available from BASF and the Tergitol R surfactants are commercially available from UNION CARBIDE.

Suitable anionic surfactants to be used herein include water soluble salts or acids of the formula $ROSO_3M$ wherein R is preferably a $C_6$–$C_{24}$ hydrocarbyl, preferably an alkyl or hydroxyalkyl having a $C_8$–$C_{20}$ alkyl component, more preferably a $C_8$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethylammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyldiphenyl-ether-sulphonates and alkylcarboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO$—M+ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use herein are the alkyl benzene sulfonates, alkyl sulfates, alkyl alkoxylated sulfates, paraffin sulfonates and mixtures thereof.

The internal disinfecting polar phase according to the present invention has a pH of from 1 to 12, preferably from 3 to 10, and more preferably from 3 to 9. The pH can be adjusted by using alkalinizing agents or acidifying agents. Examples of alkalinizing agents are alkali metal hydroxides, such as potassium and/or sodium hydroxide, or alkali metal oxides such as sodium and/or potassium oxide. Examples of acidifying agents are organic or inorganic acids such as citric or sulfuric acid.

Solvents may be present in the internal disinfecting polar phase according to the present invention. These solvents will, advantageously, give an enhanced cleaning to the disinfecting wipes 8 of the present invention. Suitable solvents for incorporation herein include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol and mixture thereof. Preferred solvents for use herein are n-butoxypropoxypropanol, butyl carbitol® and mixtures thereof. A most preferred solvent for use herein is butyl carbitol®.

The internal disinfecting polar phase herein may further comprise other optional ingredients including radical scavengers, chelating agents, thickeners, builders, buffers, stabilizers, bleach activators, soil suspenders, dye transfer agents, brighteners, anti dusting agents, enzymes, dispersant, dye transfer inhibitors, pigments, perfumes, and dyes and the like.

Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxytoluene, hydroquinone (HQ), di-tert-butyl hydroquinone (DTBHQ), mono-tert-butyl hydroquinone (MTBHQ), tert-butyl-hydroxy anysole, p-hydroxyanysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl) butane, tert-butyl-hydroxy-anyline, p-hydroxy anyline as well as n-propyl-gallate. Highly preferred for use herein is di-tert-butyl hydroxy toluene, which is for example commercially available from SHELL under the trade name IONOL CP®.

Typically, the radical scavenger, or a mixture thereof, is present in the internal water phase up to a level of 5% by weight, preferably from 0.001% to 3% by weight, and more preferably from 0.001% to 1.5%.

Suitable chelating agents to be used herein may be any chelating agent known to those skilled in the art such as the ones selected from the group consisting of phosphonate chelating agents, amino carboxylate chelating agents or other carboxylate chelating agents, or polyfunctionally-substituted aromatic chelating agents and mixtures thereof.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelating agents are commercially available from Monsanto under the trade name DEQUEST®.

Polyfunctionally-substituted aromatic chelating agents may also be useful herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetate, diethylene triamine pentaacetate, diethylene triamine pentaacetate (DTPA), N-hydroxyethylethylenediamine triacetate, nitrilotri-acetate, ethylenediamine tetraprorionate, triethylenetetraaminehexa-acetate, ethanoldiglycine, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, dipicolinic acid and derivatives thereof, or mixtures thereof.

Typically, the chelating agent, or a mixture thereof, is present in the internal polar phase at a level of from 0.001% to 5% by weight, preferably from 0.001% to 3% by weight and more preferably from 0.001% to 1.5%.

The disinfecting wipes 8 according to the present invention are suitable for disinfecting various surfaces including animate surfaces (e.g. human skin) as well as inanimate surfaces including any hard-surfaces.

Regardless of its composition, the internal polar phase will preferably comprise from about 67 to about 92% of the emulsion 12. Most preferably, the internal polar phase will comprise from about 82 to about 91% of the emulsion 12.

Where the internal polar phase comprises water as a major component, the internal phase can comprise water-soluble or dispersible materials that do not adversely affect the stability of the high internal phase inverse emulsion 12. One such material that is typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the internal water phase.

Other water-soluble or dispersible materials that can be present in the internal polar phase include thickeners and viscosity modifiers. Suitable thickeners and viscosity modifiers include polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Again, where water is a major constituent of the internal polar phase, water-soluble or dispersible materials that can be present in the internal phase include polycationic polymers to provide steric stabilization at the polar phase-lipid phase interface and nonionic polymers that also stabilize the emulsion 12. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the polar phase.

3. Emulsifier

Another key component of the high internal phase inverse emulsion 12 of the present invention is an emulsifier. In the emulsions 12 of the present invention, the emulsifier is included in an effective amount. What constitutes an "effective amount" will depend on a number of factors including the respective amounts of the lipid and internal polar phase components, the type of emulsifier used, the level of impurities present in the emulsifier, and like factors. Typically, the emulsifier comprises from about 1 to about 10% of the emulsion 12. Preferably, the emulsifier will comprise from about 3 to about 6% of the emulsion 12. Most preferably, the emulsifier will comprise from about 4 to about 5% of the emulsion 12. While the singular "emulsifier" is used to describe this component, more than one emulsifier may be used when forming the emulsion 12. Indeed, as discussed below, it may be desirable to utilize both a primary and a secondary emulsifier when certain materials are employed.

Though not intended to limit the scope of the invention, where two emulsifiers are utilized, preferred is where the primary emulsifier comprises from about 1 to about 7%, more preferably from about 2 to about 5%, most preferably from about 2 to about 4%, by weight of the emulsion 12; and the secondary emulsifier comprises from about 0.5 to about 3%, more preferably from about 0.75 to about 2%, most preferably from about 0.75 to about 1.5%, by weight of the emulsion 12.

The emulsifier needs to be substantially lipid-soluble or miscible with the lipid phase materials, especially at the temperatures at which the lipid material melts. It also should have a relatively low HLB value. Emulsifiers suitable for use in the present invention have HLB values typically in the range of from about 2 to about 5 and can include mixtures of different emulsifiers. Preferably, these emulsifiers will have HLB values in the range of from about 2.5 to about 3.5.

Preferred emulsifiers for use in the present invention include silicone polymer emulsifiers such as alkyl dimethicone copolyols (e.g., Dow Corning Q2-5200 laurylmethicone copolyol). Such emulsifiers are described in detail in co-pending U.S. patent application Ser. No. 08/767,120, filed Jan. 14, 1997 by L. Mackey (Case 5653C), now U.S. Pat. No. 5,765,112, which is incorporated by reference herein.

Other suitable emulsifiers are described in co-pending U.S. patent application Ser. No. 08/336,456, filed Nov. 9, 1994 by L. Mackey et al. (Case 5478), now abandoned, and U.S. patent application Ser. No. 08/761,097, filed Dec. 5, 1996 by L. Mackey et al. (Case 5478R), now U.S. Pat. No. 5,863,663, both of which are incorporated by reference herein. Emulsifiers described therein include certain sorbitan esters, preferably the sorbitan esters of $C_{16}$–$C_{22}$ saturated, unsaturated or branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65) and sorbitan dipalmitates (e.g., SPAN® 40). Laurylmethicone copolyol is a particularly preferred emulsifier for use in the present invention. Other suitable emulsifiers described therein include certain glyceryl monoesters, preferably glyceryl monoesters of $C_{16}$–$C_{22}$ saturated, unsaturated or branched chain fatty acids such as glyceryl monostearate, glyceryl monopalmitate, and glyceryl monobehenate; certain sucrose fatty acid esters, preferably sucrose esters of the $C_{12}$–$C_{22}$ saturated, unsaturated, and branched chain fatty acids such as sucrose trilaurate and sucrose distearate (e.g., Crodesta® F10), and certain polyglycerol esters of $C_{16}$–$C_{22}$ saturated, unsaturated or branched fatty acids such as diglycerol monooleate and tetraglycerol monooleate. In addition to these primary emulsifiers, coemulsifiers can be used to provide additional water-in-lipid emulsion 12 stability. Suitable coemulsifiers include phosphatidyl cholines and phosphatidyl choline-containing compositions such as the lecithins; long chain $C_{16}$–$C_{22}$ fatty acid salts such as sodium stearate, long chain $C_{16}$–$C_{22}$ dialiphatic, short chain $C_1$–$C_4$ dialiphatic quaternary ammonium salts such as ditallow dimethyl ammonium chloride and ditallow dimethyl ammonium methylsulfate; long chain $C_{16}$–$C_{22}$ dialkoyl(alkenoyl)-2-hydroxyethyl, short chain $C_1$–$C_4$ dialiphatic quaternary ammonium salts such as ditallowoyl-2-hydroxyethyl dimethyl ammonium chloride, the long chain $C_{16}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain $C_1$–$C_4$ dialiphatic, long chain $C_{16}$–$C_{22}$ monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries). Interfacial tension modifiers such as cetyl and stearyl alcohol for closer packing at the water-lipid interface can also be included.

Other emulsifiers useful in making the articles of the present invention include the high viscosity emulsifiers described in co-pending U.S. patent application Ser. No. 08/759,547, filed Dec. 5, 1996 by L. Mackey and B. Hird, now U.S. Pat. No. 5,980,922, which is incorporated by reference herein. These emulsifiers preferably have a viscosity at 55° C. of at least about 500 centipoise. (Viscosity can be measured using a Lab-Line Instruments Brookfield-type rotating disc viscometer.) That application describes specifically the use of emulsifiers such as those designated by The Lubrizol Corporation (Wickliffe, Ohio) as OS-122102, OS-121863, OS-121864, OS-80541J and OS-80691J, which are reaction products of (i) a hydrocarbyl-substituted carboxylic acid or anhydride (preferably a polyisobutylene-substituted succinic acid or anhydride); and (ii) an amine or alcohol, to form an ester or amide product. The materials, and methods for their manufacture, are described in U.S. Pat. No. 4,708,753, issued Nov. 24, 1987 to Forsberg [see especially Column 3, lines 32–38; and Column 8, line 10, to Column 26, line 68], and U.S. Pat. No. 4,844,756, issued Jul. 4, 1989 to Forsberg, both of which are incorporated by reference herein.

Other materials believed to be useful in the present invention include hydrocarbon-substituted succinic anhydrides such as those described in U.S. Pat. No. 3,215,707, issued Nov. 2, 1965 to Rense; U.S. Pat. No. 3,231,587, issued Jan. 25, 1996 to Rense; U.S. Pat. No. 5,047,175, issued to Forsberg on Sep. 10, 1991; and World Patent Publication Number WO 87/03613, published by Forsberg on Jun. 18, 1987. These publications are all incorporated by reference herein.

Still other materials useful as the emulsifier, particularly as a co-emulsifier with a high viscosity primary emulsifier, are ABA block copolymers of 12-hydroxystearic acid and polyethylene oxide. Such materials are described in U.S. Pat. No. 4,875,927, issued to T. Tadros on Oct. 24, 1989, which is incorporated by reference herein. A representative material of this class useful as an emulsifier herein is available from Imperial Chemical Industries PLC as Arlacel P135.

While all the above-described materials may be used as a single emulsifier, it may be desired to employ more than one emulsifier when forming the emulsion 12. In particular, where a high viscosity emulsifier is used, a certain "tacky" feel may result when the treated article is subjected to in-use shear pressures that break the emulsion 12. In this case, it may be desirable to use a relatively lower viscosity co-emulsifier with the primary emulsifier, to allow use of a lower amount of the main emulsifier, thereby alleviating tackiness. In one preferred embodiment of the present invention, a primary emulsifier available from Lubrizol (i.e., reaction product of polyisobutylene-substituted succinic acid and an amine) and a secondary emulsifier that is an ABA block copolymer of poly-12-hydroxystearic acid and polyethylene oxide (e.g., ICI's Arlacel P135) are used to provide an emulsion 12 with improved water retention levels over time, as well as beneficial reduced tackiness (via reduction in level of primary emulsifier). The skilled artisan will recognize that different desired end-uses will dictate whether multiple emulsifiers are appropriate, and the appropriate relative amounts of each if appropriate. Such a determination will require only routine experimentation by the skilled artisan in view of the present disclosure.

4. Optional Emulsion Components

The high internal phase inverse emulsions 12 of the present invention can also comprise other optional components typically present in moisture containing solutions of this type. These optional components can be present in either the continuous lipid phase or the internal polar phase and include perfumes, antimicrobial (e.g., antibacterial) actives, pharmaceutical actives, deodorants, opacifiers, astringents, skin moisturizers, and the like, as well as mixtures of these components. All of these materials are well known in the art as additives for such formulations and can be employed in effective, appropriate amounts in the emulsions 12 of the present invention. A particularly preferred optional component that is included in the emulsions 12 of wet-like cleansing wipes 8 according to the present invention is glycerin as a skin conditioning agent.

The emulsion 12 component of the articles of the present invention is described and claimed herein in terms of components, and corresponding amounts of the components, that are present after emulsion 12 formation. That is, when the stable emulsion 12 is formed and applied to the carrier. It is understood that the description (components and amounts) of the emulsion 12 also encompasses emulsions 12 formed by combining the described components and levels, regardless of the chemical identity of the components after emulsification and application to the carrier.

C. Other Optional Article Components

Besides the high internal phase inverse emulsion 12, there are other optional components that can be included in the articles of the present invention, typically for the purpose of improving the cleaning performance of the article when the internal polar phase of the emulsion 12 is released. Certain of these optional components cannot be present in the emulsion 12 at significant levels (e.g., greater than 2% of the internal phase) because they can cause premature disruption of the emulsion 12. These include various anionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, ampholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion 12. For example, an aqueous solution of these high HLB detergent surfactants can be applied to the carrier either before or after application of the emulsion 12 to the carrier. During wiping, the emulsion 12 is disrupted, releasing the polar phase components so that they can then be combined with the high HLB detergent surfactant to provide improved hard surface cleaning.

Though the description of the invention generally relates to applying a single water-in-lipid emulsion 12 to the carrier, it is recognized that two or more different emulsions 12 may be utilized in preparing a single article. In such embodiments, the emulsions 12 may differ in a variety of ways, including but not limited to, the ratio of the internal polar phase and the external lipid phase, the emulsifiers used, the components used for either or both of the internal and lipid phases, and the like. Utilization of multiple emulsions 12 in one article may be particularly desirable when two or more components are incompatible with each other, but can each be included in a separate emulsion 12. Alternatively, if a particular reaction is desired at the time of use, the reactants can be provided in separate emulsions 12. Upon shearing of the emulsions 12 during use, the desired reaction will occur. For example, where foaming is desired during the wiping processes, a mild acid can be incorporated in the internal polar phase of one emulsion 12, while bicarbonate is incorporated in the internal polar phase of a second emulsion 12. Upon shearing of the emulsions 12 during use, the reactants interact to provide the desired foam.

Suitable emulsion 12 descriptions are also found in the aforementioned commonly assigned World Patent Applications WO 96/14835, published May 23, 1996, in the names of Mackey et al.; and WO 96/21505, published Jul. 18, 1996, in the name of DesMarais, incorporated herein by reference.

The Pattern

As noted above, the emulsion 12 is preferably applied to the substrate 10 in a discontinuous pattern. As noted above, a discontinuous pattern is one in which the emulsion 12 has distinct regions separated by regions 14 of the substrate 10 which are free of the emulsion 12. Suitable discontinuous patterns comprise discrete island regions of the emulsion 12, essentially continuous networks of emulsion 12, discrete macropatterns of the emulsion 12, and, preferably, discrete stripes of the emulsion 12 disposed in a semi-continuous pattern. The stripes are preferably continuous, as illustrated, but may, alternatively, comprise a pattern of discrete segments which collectively comprise a stripe. If stripes are selected, the stripes are preferably oriented in the machine direction, for ease of manufacture.

The emulsion 12 may be applied to and disposed on the substrate 10 by any suitable means well known in the art, such as gravure printing, flexographic printing, spraying, and preferably extruding. More preferably, the emulsion 12 is extruded as a series of continuous cylindrically shaped beads. A continuous cylindrical shape is preferred for the emulsion 12 because this shape reduces the surface area to volume ratio of the emulsion 12.

The stripes may be straight, as shown, may be sinusoidally shaped, etc. If sinusoidally shaped stripes are selected, preferably the stripes are in phase, so that parallelism is maintained and each stripe remains equally spaced from the adjacent stripes.

It is desired that the emulsion 12 have the minimum possible surface area to volume ratio. Minimizing the surface area to volume ratio reduces water loss from the emulsion 12 due to evaporation. Preferably the emulsion 12 has a surface area to volume ratio of less than or equal to 4/unit length, more preferably less than or equal to 3/unit length, and most preferably less than or equal to 2/unit length, wherein the unit length is measured in the cross section of the emulsion 12. Suitable surface area to volume ratios for cylindrical beads of emulsion 12 range from 40 to 200 inches$^{-1}$ and preferably 75 to 125 inches$^{-1}$.

However, the optimum results are not achieved, for example, by presenting a single, unitary sphere of emulsion 12 to the user with the wipe 8. Such an arrangement would likely provide adequate water. However, the water distribution would be highly localized and may not adequately spread throughout the surface area of the wipe 8. Preferably, the distribution of the emulsion 12, or, more particularly, the water released therefrom, approximates the perception of a water spray onto the skin.

It will be apparent to one skilled in the art that as the basis weight and absorbency of the substrate 10 increase, the amount of water necessary to locally saturate the substrate 10 will likewise increase. Therefore, as the basis weight and/or absorbency of the substrate 10 increases, the amount of emulsion 12 applied to the substrate 10 should increase proportionately.

Preferably, 5 to 35 percent, and more preferably 10 to 25 percent of the surface area of the wipe 8 has emulsion 12 disposed thereon. Upon rupture, the emulsion 12 locally wets corresponding regions of the substrate 10. The wetted portion of the substrate 10 may range from 10 to 90 percent of the surface area of the substrate 10, with, of course, the balance of the surface area of the substrate 10 remaining dry due to the discontinuous pattern.

It will be apparent that in use the percentage of wetted surface area will be greater than the percentage of surface area initially coated by the emulsion 12. It is to be further understood that, of course, the entire wipe 8 may be wetted as a function of the time and/or use of the wipe 8.

Thus, beads of emulsion 12 are preferably applied to the substrate 10 in an arrangement that accommodates both the diameter and pitch of the beads in a preferred geometry. The amount of water carried by the emulsion 12 increases according to the square of the diameter of the beads. Therefore, as the diameter of the beads increases, the pitch between adjacent stripes of emulsion 12 should likewise increase. Suitable pitches between adjacent beads of emulsion range from 0.030 to 1.500 inches, and preferably from 0.175 to 0.375 inches.

If the emulsion 12 is to be directly exposed to the surface, i.e., disposed on the outside of the substrate 10 as the wipe 8 is presented to the user, the emulsion 12 preferably comprises a level at least 25 percent, more preferably at least 50 percent, and most preferably at least 75 percent of that of the basis weight of the substrate 10. Alternatively, if the emulsion 12 is disposed between two-plies of substrate 10 in a laminate construction, for tissue applications, preferably the emulsion 12 comprises at least 150 percent, more preferably at least 200 percent, and most preferably at least 250 percent of the combined basis weight of the two plies. In such a laminate construction for hard surface cleaning applications, preferably the emulsion 12 comprises at least 500 percent, more preferably at least 650 percent, and most preferably at least 800 percent of the combined basis weight of the two plies.

It is to be noted that the basis weights described herein refer to the overall basis weight of the substrate 10, as an average of the various different basis weight regions contained within the substrate 10. The basis weight of the substrate 10 may be measured according to ASTM Test Method D3776-9, which test method is incorporated herein by reference, with results reported in pounds per 3,000 square feet. The emulsion 12 weight is gravimetrically measured once the basis weight of the substrate 10 is known, as the tare.

If desired, the regions 14 of the substrate 10 free of the emulsion 12 may be slightly wider in the cross machine direction at the edges of the wipe 8 than the corresponding regions 14 disposed at the interior of the wipe 8. This arrangement accommodates processing and slitting of a wide, multi-roll position web of the wipe 8 into narrower discrete units for transport and sale to the consumer. It will be apparent to one skilled in the art that the regions 14 free of the substrate may form a border at the other edges of the wipe 8 as well. Such a geometry can easily be accomplished by not applying the emulsion 12 continuously. Instead, the emulsion 12 may be intermittently applied in the machine direction. The substrate 10 is then cut or perforated in the cross machine direction coincident the regions 14 free of the emulsion 12 in order to yield discrete or separable wipes 8.

Figure 2:
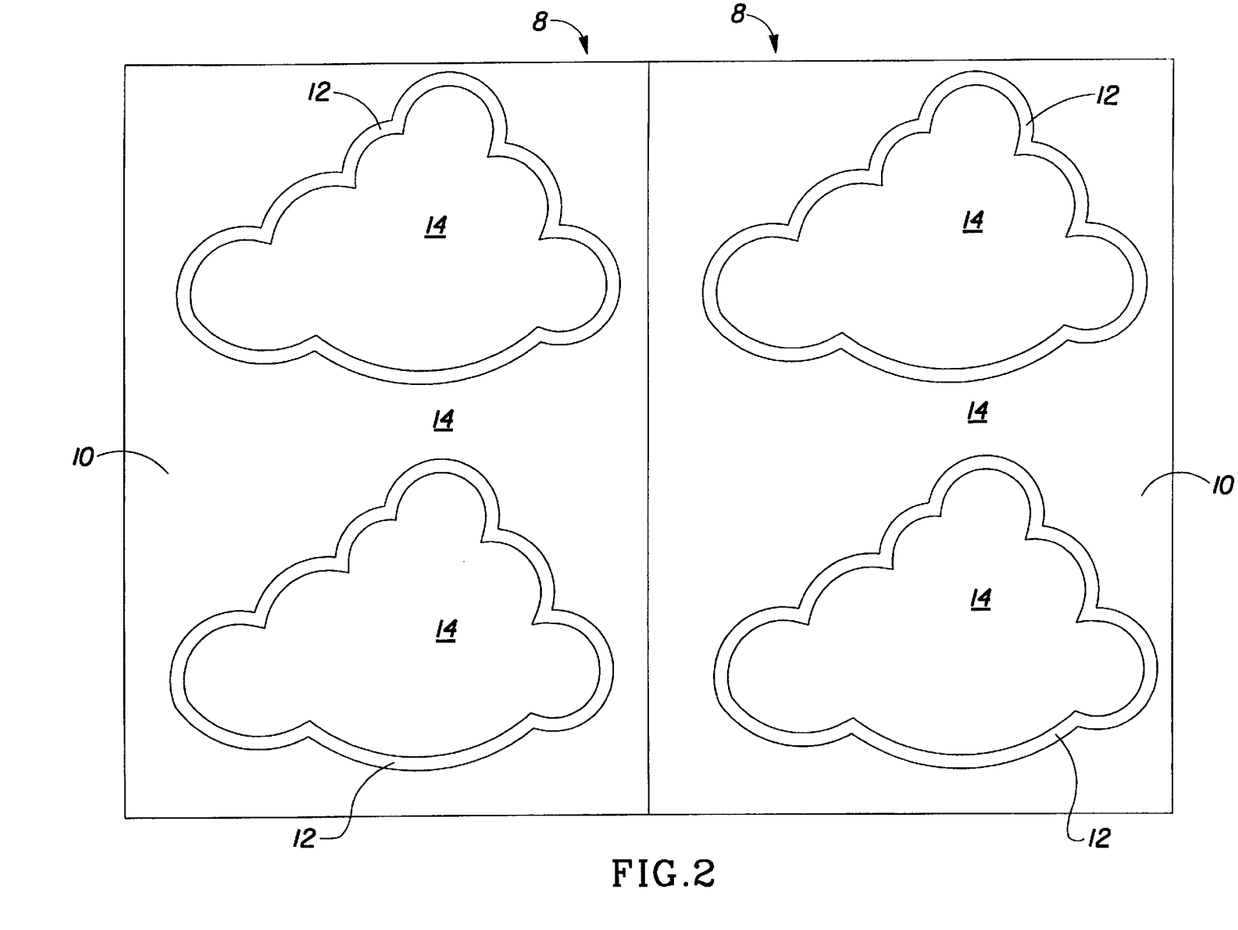
FIG. 2 is a top plan view of an alternative embodiment according to the present invention comprising macropatterns of emulsion defining decorative indicia.

Referring to FIG. 2, the emulsion 12 may define decorative indicia such as macropatterns. The macropatterns may be used above, as shown, or may be superimposed on the discontinuous stripe pattern of emulsion 12. Macropatterns of emulsion 12 provide the advantage that locally heavier loadings of water can be applied from a pattern that provides an aethetically pleasing visual cue to the user of where the emulsion 12 is present. Macropatterns of emulsion 12 may form decorative indicia. Such decorative indicia may be provided in the form of flowers, butterflies, clouds, tradenames, advertising, or any other planar pattern envisioned by the user.

In a preferred embodiment, the substrate 10 comprises a multi-basis weight tissue. A multi-basis weight substrate 10 may be made according to the aforementioned patents describing the same and incorporated by reference hereinabove. A multi-basis weight substrate 10 provides the advantage that excess water will more easily saturate the low basis weight regions and, therefore, be more readily applied to the surface. Preferably the multi-basis weight substrate 10 comprises an essentially continuous high basis weight network region with discrete low basis weight regions distributed throughout the essentially continuous network.

Alternatively, a substrate 10 having a semi-continuous pattern of high and low basis weight regions may be selected. In yet a less preferred embodiment, a substrate 10 having an essentially continuous network of low basis weight regions with discrete high basis weight regions distributed therein may be utilized, provided, however, one is willing to accept the strength tradeoff inherent in such a substrate 10. Such a substrate 10, prophetically, provides the benefit that the essentially continuous pattern of low basis weight regions will more readily allow water expressed from the emulsion 12 to penetrate the substrate 10 and be transferred to the surface.

If a substrate 10 having an essentially continuous high basis weight region is selected, preferably the pitch of the discrete low basis weight regions is less than the pitch between adjacent stripes of the emulsion 12. This relative difference in pitches assures that the emulsion 12 will intercept the low basis weight regions and be more readily transmitted therethrough, as described above.

For the embodiments described herein for tissue applications, a substrate 10 having a basis weight of 7 to 10 pounds per 3,000 square feet per ply and 50 to 300, and more preferably 100 to 200 discrete low basis weight regions per square inch is suitable. For hard surface cleaning applications, a substrate 10 having a basis weight of 20 pounds per 3,000 square feet and 100 to 200 discrete low basis weight regions per square inch is suitable.

In a preferred embodiment, the wipe 8 may be made according to commonly assigned U.S. Application entitled "Cleaning Articles Comprising a Cellulosic Fibrous Structure Having Discrete Basis Weight Regions Treated with A High Internal Phase Inverse Emulsion" filed Jul. 1, 1997, in the names of Nicholas J. Nissing et al., U.S. patent application Ser. No. 08/886,764, pending, the disclosure of which patent is incorporated herein by reference.

If a substrate 10 having a semi-continuous basis weight pattern is selected, such a substrate 10 may be made according to commonly assigned U.S. Pat. No. 5,628,876, issued May 13, 1997 to Ayers et al., and incorporated herein by reference. Preferably, the semi-continuous pattern is oriented in the machine direction. If such a geometry is selected, prophetically, the beads of emulsion 12 may be applied to the semi-continuous patterned substrate 10 such that the emulsion 12 is juxtaposed with, and preferably coincident, the low basis weight regions of the substrate 10. This arrangement provides the advantage, discussed above, that the water expressed from the emulsion 12 is more readily transmitted through the low basis weight regions of the semi-continuous patterned substrate 10. The low basis weight regions of the semi-continuous pattern, if parallel to the machine direction, may be disposed on a pitch less than or equal to the stripes of the emulsion 12.

It will be apparent to one skilled in the art that many variations are feasible and within the scope of the claimed invention. For example, a laminate construction comprising emulsion 12 disposed between two plies of substrate 10 may be made as described above. It is not necessary, however, that the plies be identical. One ply may be a nonwoven for strength. The other ply may be a tissue to provide for transmission of the water to the surface. If desired, the nonwoven ply may be treated to render it hydrophobic and thereby ensure that the water released from the emulsion 12 is transferred to the surface via the tissue ply.

Alternatively, a laminate comprising two tissue plies may be selected. One of the plies may have a multi-basis weight region pattern described above. The multi-basis weight region may comprise a semi-continuous pattern. The other ply may comprise a single basis weight region for strength. This embodiment provides for greater transmission of water through one of the plies than through the other ply. Alternatively, the multi-basis weight region ply may comprise an essentially continuous network of high basis weight regions with discrete low basis weight regions distributed therein.

In yet another embodiment, a laminate having a plurality of several laminae may be provided. The laminae may comprise alternating plies of substrate 10 and emulsion 12. Such a laminate may have two outwardly facing substrate 10 laminae as described above. The emulsion 12 may be wholly contained within the laminate. Alternatively, emulsion 12 may be disposed on one exposed surface of such a laminate.

Figure 3:
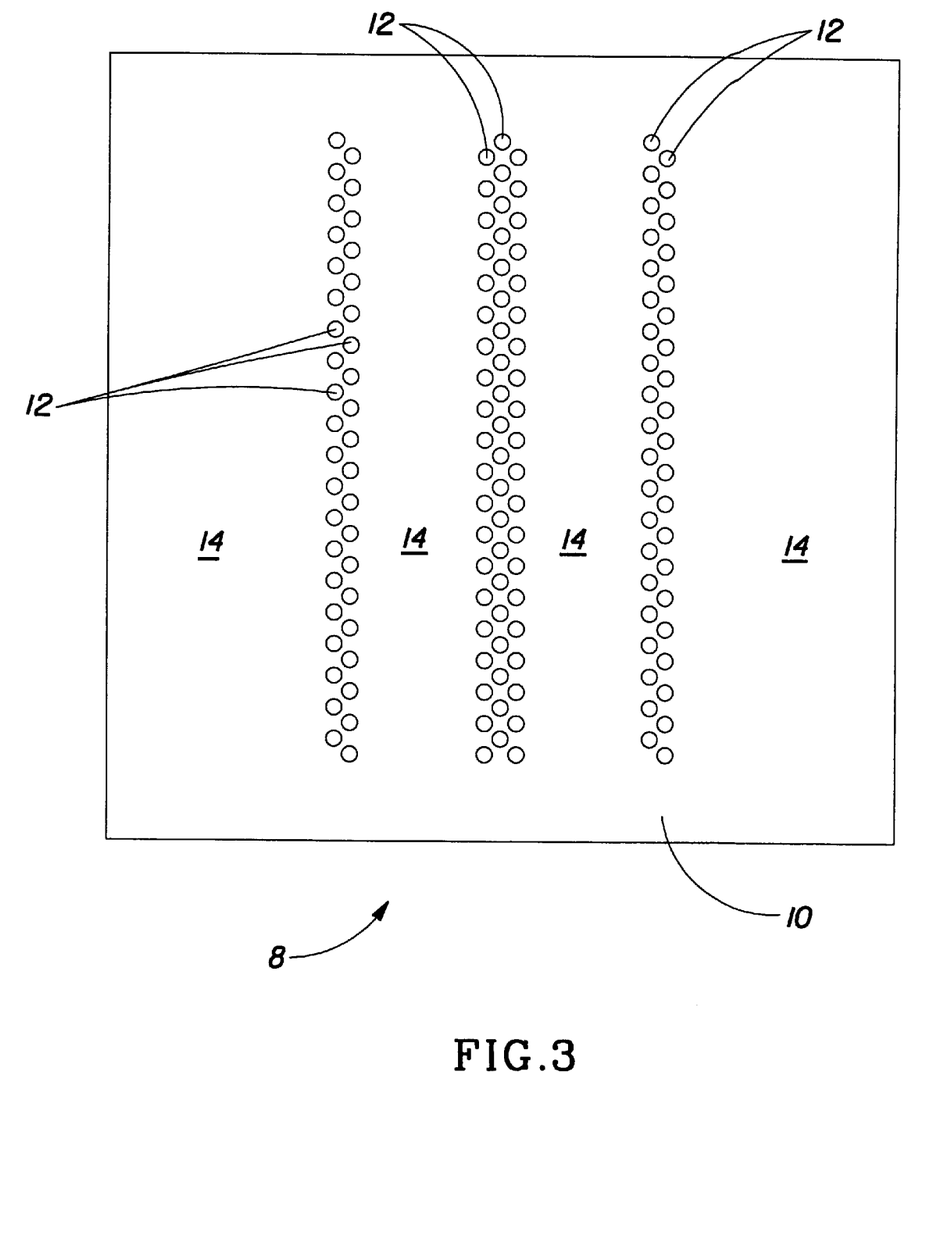
FIG. 3 is a top plan view of an alternative embodiment according to the present invention showing a pattern wherein the stripes are defined by discrete juxtaposed spheres of emulsion.

Referring to FIG. 3, in yet another embodiment stripes of emulsion 12 may be comprised of discrete spheres of emulsion 12. The discrete spheres of emulsion 12 are juxtaposed to collectively form the discontinuous pattern. This arrangement provides the advantage of a suitable surface area to volume ratio, similar to the generally cylindrically shaped beads described above. Although stripes are illustrated in FIG. 3, one of ordinary skill will understand that discrete spheres of emulsion 12 may be juxtaposed to form any discontinuous pattern desired.

Yet another variation, illustrated by FIG. 3 but applicable to any of the foregoing embodiments, is to vary the amount of the emulsion 12 within the discontinuous pattern. For example, certain stripes of emulsion 12 may have relatively more emulsion 12 than other stripes. This arrangement allows for locally heavier loading of the water onto the surface to be cleaned, but yet still provides relatively drier edges to minimize the amount of residual water left on the surface.

It will be apparent that, depending upon the desired application, the wipes 8 may be provided as discrete units, may be joined in seiatum by perforations, etc. The wipes 8 may be individually dispensed, such as is commonly done for facial tissues. If individual dispensing is desired, the wipes may be provided in either a reach-in or pop up dispenser, as disclosed in commonly assigned U.S. Pat. No. 4,623,074 issued Nov. 8, 1986 to Dearwester; U.S. Pat. No. 5,520,308 issued May 28, 1996 to Berg. Jr. et al. and U.S. Pat. No. 5,516,001 issued May 14, 1996 to Muckenfuhs et al., the disclosures of which are incorporated herein by reference. Alternatively, the wipes 8 may be core-wound, as disclosed in commonly assigned U.S. Pat. No. 5,318,235, issued Jun. 7, 1994 to Sato, the disclosure of which is incorporated herein by reference. If desired, the wipes 8 may be lightly compressed for packaging, provided care is taken not to rupture the emulsion 12. Such packaging may be accomplished as disclosed in commonly assigned U.S. Pat. No. 5,664,897, issued Jul. 8, 1997 to Young et al., the disclosure of which is incorporated herein by reference.

What is claimed is:

1. A wipe comprising a laminate having a plurality of laminae, said laminae comprising two outer plies and a central ply disposed therebetween, each of said outer plies comprising a substrate, said central ply being disposed on at least one of said outer plies, said central ply comprising a high internal phase inverse emulsion disposed in a pattern comprising discrete macro-patterns or discrete stripes, said outer plies having a combined first basis weight, said emulsion having a coating weight, said coating weight being at least 150 percent of said combined basis weight of said outer plies, said emulsion further having a surface area to volume ratio of less than 200 inches$^{-1}$.

2. A wipe according to claim 1 wherein said coating weight of said emulsion is at least 200 percent of said combined basis weight of said outer plies.

3. A process for making a wipe, said process comprising the steps of:

providing a substrate;

providing a high internal phase inverse emulsion;

disposing said emulsion on said substrate in a pattern whereby a first plurality of regions of said substrate is coated with said emulsion, said emulsion comprising a plurality of sinusoidally shaped stripes and a second plurality of regions of said substrate is free of said emulsion.

4. A process according to claim 3 wherein said step of disposing said emulsion on said substrate comprises:

moving one of said substrate and said emulsion relative to the other in a machine direction; and extruding said emulsion onto said substrate in a plurality of stripes, said stripes being generally parallel said machine direction.

5. A process according to claim 4 wherein said emulsion has a surface area to volume ratio greater than 50 inches$^{-1}$.

6. A process according to claim 4 wherein said emulsion covers from 10 to 25 percent of the surface area of said substrate.

7. A wipe comprising two outer plies, each of said outer plies comprising a substrate, said wipe further comprising a high internal phase inverse emulsion disposed between said outer plies, wherein said emulsion is disposed in a plurality of sinusoidal stripes.

8. A wipe according to claim 7 wherein said emulsion is disposed in a plurality of parallel stripes.

9. A wipe according to claim 8 wherein said emulsion has a surface area to volume ratio less than or equal to 4/unit length.

10. A wipe according to claim 8 wherein at least one said ply comprises cellulose.

11. A wipe according to claim 10 wherein both said plies comprise cellulose.

\* \* \* \* \*